United States Patent [19]
DesJardin et al.

[11] Patent Number: 4,713,460
[45] Date of Patent: Dec. 15, 1987

[54] 2,3-BIS-(POLY)(CHLOROMETHYL)PYRI-
DINES

[75] Inventors: Michael A. DesJardin, Dublin;
Thomas J. Dietsche, Berkeley; Jon A. Orvik, Walnut Creek, all of Calif.

[73] Assignee: The Dow Chemical Company, Midland, Mich.

[21] Appl. No.: 888,897

[22] Filed: Jul. 22, 1986

[51] Int. Cl.$^4$ .................. C07D 211/72; C07D 211/84
[52] U.S. Cl. ...................... 546/345; 546/346
[58] Field of Search ............................... 546/345, 346

[56] References Cited

U.S. PATENT DOCUMENTS

| | | | |
|---|---|---|---|
| 3,317,549 | 5/1967 | Johnston | 546/345 |
| 3,420,833 | 1/1969 | Taplin | 546/345 |
| 3,709,894 | 1/1973 | Klemm et al. | 546/345 |
| 4,504,665 | 3/1985 | Haga et al. | 546/345 |
| 4,507,486 | 3/1985 | Marinak et al. | 546/345 |

OTHER PUBLICATIONS

Kakimoto et al., Bulletin Chem. Soc. Japan, vol. 42, 2996–2997.
Ruhoff, Org. Syn., Coll. vol. 2, 315 (1943).
Paul et al., Aus. J. Chem., 22, 1759–72 (1969).
Sam et al., J. Am. Chem. Soc., 94, 4024 (1972).
Tsuda, CA, 50, 13895f.
Klemm et al., J. Het. Chem., 7, 463–4, (1970).
Klemm et al., J. Het. Chem., 9, 843–8, (1972).
Reutgers-Nease, Chem. & Eng. News, p. 32, Mar. 31, 1966.
Paul et al., Aus. J. Chem., 21, 1291–1310, (1968).

*Primary Examiner*—Henry R. Jiles
*Assistant Examiner*—Robert C. Whittenbaugh

[57] ABSTRACT

Novel 2,3-bis((poly)chloromethyl)pyridines and 3,6-dichloro-2-(polychloromethyl)pyridines were obtained by vapor phase chlorination of 2,3-lutidine. Chlorination at about 350° C. using a 14.4 sec. residence time and a chlorine to 2,3-lutidine mole ratio of about 6.8, for example, produced 2-(chloromethyl)-3-(dichloromethyl) pyridine, 3-(chloromethyl)-2-(dichloromethyl)pyridine, 2,3-bis(dichloromethyl)pyridine, 6-chloro-2,3-bis(dichloromethyl)pyridine, 3-(dichloromethyl)-2-(trichloromethyl)pyridine, 6-chloro-3-(dichloromethyl-2-(trichloromethyl)pyridine, 6-chloro-2-(dichloromethyl)-3-(trichloromethyl)pyridine, and 3,6-dichloro-2-(trichloromethyl)pyridine. The compounds are useful as starting materials for herbicides and pharmaceutical agents.

25 Claims, No Drawings

2,3-BIS-(POLY)(CHLOROMETHYL)PYRIDINES

BACKGROUND OF THE INVENTION 2,3-Bis((poly)chloromethyl)pyridines are derivatives of 2,3-lutidine in which the methyl groups have been converted into partially or completely chlorinated forms; viz., into mono-, di-, or trichloromethyl moieties. Such derivatives, which can be considered to be partially oxidized derivatives of 2,3-lutidine, if known and available, could be utilized in the preparation of useful herbicides, such as the 2-(2-imidazolin-2-yl)pyridine herbicides reported in published European Patent Application 0,041,623, and pharmaceuticals, such as the 7,8-dihydropyrido[2,3-d]pyridazin-5(6H)-one antituberculous compounds reported in Bull Chem. Soc. Japan, 42, 2996–2997 (1969).

3,6-Dichloro-2-((poly)chloromethyl)pyridines are known and have been employed in the preparation of 3,6-dichloropicolinic acid, a commercial herbicide (U.S. Pat. No. 3,317,549). Known methods for the preparation of 3,6-dichloro-2-(polychloromethyl)pyridines by the chlorination of alpha picoline are not completely satisfactory because such chlorinations are not highly selective and consequently produce many isomers and other chlorinated compounds as by-products.

SUMMARY OF THE INVENTION

It has now been found that 2-mono and 2,3-bis((poly)chloromethyl)pyridines can be prepared by the vapor phase chlorination of 2,3-lutidine.

Thus, 2-mono and 2,3-bis((poly)chloromethyl)pyridines of Formula I

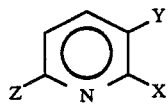

wherein
X represents $CH_2Cl$, $CHCl_2$, or $CCl_3$;
Y represents chloro, $CH_2Cl$, $CHCl_2$, or $CCl_3$; and
Z represents hydrogen or chloro;
with the proviso that
(a) X and Y cannot both represent $CH_2Cl$ or $CCl_3$, and
(b) X represents $CHCl_2$ or $CCl_3$ and Z represents chloro when Y represents chloro
are prepared by contacting 2,3-lutidine with chlorine in the presence of a chlorocarbon diluent in the vapor phase under conditions conducive to the reaction.

The 2,3-bis((poly)chloromethyl)pyridine compounds of Formula I prepared in the process disclosed hereinabove; that is, compounds of Formula II

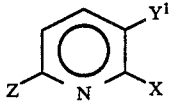

wherein
X and $Y^1$ each, independently, represents $CH_2Cl$, $CHCl_2$, or $CCl_3$; and
Z represents hydrogen or chloro;
with the proviso that X and $Y^1$ cannot both represent $CH_2Cl$ or $CCl_{13}$
are novel.

The compounds of Formulae I and II are useful as intermediates in the preparation of herbicides and pharmaceutical agents.

DETAILED DESCRIPTION OF THE INVENTION

The 2-mono and 2,3-bis((poly)chloromethyl)pyridine compounds of Formula I are obtained by the vapor phase chlorination of 2,3-lutidine. The reaction is carried out in a manner similar to that described for the chlorination of aromatic, heterocyclic nitrogen compounds in general in U.S. Pat. No. 3,420,833, which description is hereby incorporated by reference. In the present invention 2,3-lutidine, a chlorocarbon solvent or diluent, and an excess of chlorine are vaporized and fed simultaneously to a continuous vapor phase reactor at an elevated temperature in a manner that ensures good mixing and the product effluent from the reactor is condensed and collected. Reaction temperatures of about 250° to about 550° C. are useful and temperatures of about 300° to about 450° C. are preferred. Contact times of about 5 to about 120 seconds are suitable while times of about 10 to about 30 seconds are preferred. Chlorine to 2,3-lutidine mole ratios of about 4 to about 16 are useful while mole ratios of about 6 to about 12 are preferred, and chlorocarbon solvent or diluent to 2,3-lutidine weight ratios of about 2 to about 50 are suitable while weight ratios of about 4 to about 30 are preferred.

Any chlorocarbon diluent that is stable under the reaction conditions, such as carbon tetrachloride, perchloroethylene, and the like, can be employed. Carbon tetrachloride is preferred. It is further preferred to feed the 2,3-lutidine to the reactor as a solution in the chlorocarbon solvent or diluent. Other inert diluents such as nitrogen, argon, helium, and the like can be employed in addition to the chlorocarbon.

The compounds of Formula I can be recovered from the reaction mixtures obtained on chlorination by distilling the condensate to remove the chlorocarbon and the by-product hydrogen chloride. The compounds of Formula I are, however, generally obtained in this procedure as mixtures of several compounds of Formula I and some chloropyridine by-products. The individual compounds of Formula I can be recovered from these mixtures by conventional means such as fractional distillation, crystallization, extraction, preparative gas chromatography, preparative high pressure liquid chromatography, preparative thin layer chromatography, and the like, and combinations of these methods. For some applications, the crude reaction mixtures can be used as a starting material or intermediate, either before or after the removal of solvent and hydrogen chloride.

The compounds of Formula I are liquids or solids which can be stored for future use or can be employed immediately as starting materials or intermediates.

The compounds of Formulae I and II can be utilized to prepare useful products by employing the known reactions of $CH_2Cl$, $CHCl_2$ and $CCl_3$ moieties attached to pyridine rings, which are known to those skilled in the art and which are discussed, for example, in *Advanced Organic Chemistry: Reactions Mechanisms, and Structure* by March, *Survey of Organic Synthesis* by Buehler and Pearson, and other compendia. For example, hydrolysis gives compounds corresponding to Formulae I and II wherein X and Y represent $CH_2OH$, CHO or COOH instead of $CH_2Cl$, $CHCl_2$ or $CCl_3$.

These hydrolysis product intermediates, in turn, undergo the expected reactions of alcohols, aldehydes, and acids having similar environments, which reactions are well known to those skilled in the art.

Specifically, hydrolysis of 3,6-dichloro-2-(trichloromethyl)pyridine to 3,6-dichloropicolinic acid, a commercial herbicide, can be accomplished by hydrolysis with sulfuric acid and other strong acids as described in U.S. Pat. No. 3,317,549. 3,6-Dichloro-2-(dichloromethylpyridine), in a like manner, can be hydrolyzed to 3,6-dichloropicolinaldehyde, and this can be oxidized to 3,6-dichloropicolinic acid by conventional methods, such as with potassium permangante in benzene containing a crown ether (J. Am. Chem. Soc., 94, 4024–5 (1972)).

2-(Chloromethyl)- and 2-(dichloromethyl)-3-(trichloromethyl)pyridines can be hydrolyzed with sulfuric acid utilizing the general procedure of U.S. Pat. No. 4,504,655 to obtain 2-hydroxymethyl- and 2-formylpyridine-3-carboxylic acids, which can be converted, using conventional techniques and the methods disclosed in Aus. J. Chem. 22, 1759–72 (1969) and Bull. Chem. Soc. Japan, 42, 2996–7 (1969), to 7,8-dihydropyrido[2,3-d]pyridazin-5(6H)ones, which possess utility as antituberculous agents.

3-(Chloromethyl)- and 3-(dichloromethyl)-2-(trichloromethyl)pyridines can, in an analogous manner be converted to 3-hydroxymethyl and 3-formylpyridine-2-carboxylic acids. These in turn can be converted to herbicidal substituted 2-(2-imidazolin-2-yl)pyridines as disclosed in European Patent Application No. 0,041,623 using the methods given therein and other conventional methods.

Each of the compounds of Formula II individually or in mixtures can be converted to pyridine-2,3-dicarboxylic acid or 6-chloropyridine-2,3-dicarboxylic acid by hydrolysis, for example with sulfuric acid, and subsequent oxidation using standard techniques, such as those given in Org. Syn., Coll. Vol. 2, 315 (1943) and in J. Am. Chem. Soc., 94, 4024–5 (1972). These pyridine-2,3-dicarboxylic acids can be converted to substituted 2-(2-imidazolin-2-yl) pyridine-3-carboxylic acid herbicides using the procedures given in European Patent Application No. 0,041,623. Pyridine-2,3-dicarboxylic acid, is also an intermediate for many other other herbicides and for various pharmaceutical agents.

Each of the compounds of Formula II individually or in mixtures can additionally be further chlorinated in the liquid phase to obtain 2,3,6-trichloropyridine, 2,3,5,6-tetrachloropyridine, 2,3,4,6-tetrachloropyridine, or pentachloropyridine see Ser. No. 889,052 filed July 22, 1986. The mixture of polychloro-2,3-lutidines obtained by the present process is further chlorinated either directly or after removal of the chlorocarbon diluent in a preferred procedure.

The following examples are presented to illustrate the invention and should not be construed as limiting the scope.

EXAMPLES 1–5

A 5 weight percent solution of 2,3-lutidine in carbon tetrachloride was thermally vaporized and fed into a 5.8 liter quartz continuous flow reactor having a length to diameter ratio of 5:1. Chlorine was heated and fed to the reactor as a vapor simultaneously. The conditions employed in Examples 1–5 are given in Table I.

TABLE I

| | CHLORINATION PARAMETERS | | | | | | |
|---|---|---|---|---|---|---|---|
| EXAMPLE | REACTOR TEMP., °C. | RESIDENCE TIME, Sec. | CHLORINE INLET TEMP., °C. | 2,3-LUTIDINE INLET TEMP., °C. | CHLORINE FLOW RATE, g/min. | 2,3-LUTIDINE FLOW RATE, g/min. | MOLAR RATIO, CHLORINE to 2,3-LUTIDINE |
| 1 | 445° C. | 14.3 | 300–350 | 480–500 | 11.1 | 2.0 | 8.2 |
| 2 | 505 | 15.1 | 300 | 110–130 | 10.9 | 1.6 | 11.0 |
| 3 | 470 | 13.1 | 300 | 125–130 | 11.3 | 2.1 | 8.4 |
| 4 | 410 | 14.5 | 310–330 | 120–140 | 11.1 | 2.2 | 8.1 |
| 5 | 350 | 14.4 | 250–300 | 135–150 | 11.1 | 2.5 | 6.8 |

The output of the chlorination reactor was condensed in an ice-cooled trap attached to the outlet of the reactor. The solutions collected were analyzed by gas chromatography/mass spectrometry and capillary gas chromatography to obtain the product distributions given in Table II. The excess chlorine, carbon tetrachloride, by-product hydrogen chloride, and any other low boiling components were removed by evaporation under reduced pressure in a rotating evaporator to obtain the crude product weights of that table.

TABLE II

| | | CHLORINATION PRODUCT DISTRIBUTION | | | | | | |
|---|---|---|---|---|---|---|---|---|
| | g. PRODUCTS[1] PER | AREA PERCENT OF PRODUCTS OBTAINED[3] (NUMBER OF COMPONENTS[4]) | | | | | | |
| EXAMPLE | g. 2,3 LUTIDINE FED | $C_7H_7Cl_2N$ | $C_7H_6Cl_3N$ | $C_7H_5Cl_4N$ | $C_7H_4Cl_5N$ | $C_7H_3Cl_6N$ | $C_7H_2Cl_7N$ | $C_6H_2Cl_5N^2$ |
| 1 | 1.62 | — | — | 2.2 | 13.6(3) | 45.3(2) | 1.8(2) | 6.8 |
| 2 | 1.43 | 5.2 | 6.1(2) | 5.6 | 7.9(3) | 5.0(2) | 0.4(2) | 1.7 |
| 3 | 1.79 | 2.5(2) | 2.4(2) | 3.1 | 16.2(3) | 14.8(2) | 1.2(2) | 5.0 |
| 4 | 2.92 | — | 0.4 | 4.6 | 19.3(3) | 49.1(2) | 0.8(2) | 3.8 |
| 5 | 1.83 | 3.2(2) | 17.1(2) | 37.4(2) | 22.8(3) | 10.2(2) | 0.1(2) | 0.8 |

[1]May contain residual carbon tetrachloride.
[2]3,6-Dichloro-2-(trichloromethyl)pyridine, identified using an authentic standard.
[3]2,6-Dichloro-3-(trichloromethyl)pyridine, 2,3,6-trichlorpyridine, 2,3,4,6-tetrachloropyridine, 2,3,5,6-tetrachloropyridine and pentachloropyridine were also identified as products.
[4]Gas chromatographic peaks having the noted empirical formula as determined by mass spectrometry.

The components of Example 5 were separated by preparative thin layer chromatography of the concentrated crude product to obtain the 2,3-bis((poly)-chloromethyl)pyridine products listed in Table III. The crude sample was prepurified by dissolving it in methylene chloride, adding silica kieselgel 60PF254 to the solution and, after a short time, filtering and rinsing the insoluble materials with methylene chloride. The methylene chloride was then removed by evaporation. Utilizing a Harrison Research Model 7924T Chromatron TLC, an approximately 10 percent solution of the prepurified product in hexane was applied to a 4 mm silica kieselgel 60PF254 rotor saturated with hexane. The application area was rinsed with 2 ml of methylene chloride. Hexane (200 ml) was added to equilibrate the rotor. The products were obtained by eluting sequentially with about 325 ml hexane, about 100 ml carbon tetrachloride, a 1:1 mixture of carbon tetrachloride and methylene chloride, methylene chloride, methylene chloride containing about 1.5 percent methanol, and finally a 1:1 mixture of acetone and the methanolic methylene chloride to obtain the major components in solution. Evaporation of the solvents gave the major components in a partially purified form. These were identified by proton nuclear magnetic resonance analysis. Certain of the components were further purified by recrystallization and the melting points determined.

12. A process for preparing compounds of the formula

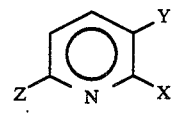

wherein
X represents $CH_2Cl$, $CHCl_2$, or $CCl_3$;
Y represents chloro; $CH_2Cl$, $CHCl_2$, or $CCl_3$; and
Z represents hydrogen or chloro;
with the proviso that
(a) X and Y cannot both represent $CH_2Cl$ or $CCl_3$ and
(b) X represents $CHCl_2$ or $CCl_3$ and Z represents chloro when Y represents chloro

TABLE III

| 2,3-BIS((POLY)CHLOROMETHYL)PYRIDINE PRODUCTS (SUBSTITUENTS REFER TO FORMULA I) | | | | |
|---|---|---|---|---|
| X | Y | Z | M.P., °C. | NMR SPECTRA ($CDCl_3$/DMSO WITH TMS REFERENCE), ppm |
| $CH_2Cl$ | $CHCl_2$ | H | | 5.02(s,2H), 7.75(s,1H), 8.35(q,1H), 7.55(q,1H), 8.65(q,1H) |
| $CHCl_2$ | $CH_2Cl$ | H | | 7.15(s,1H), 4.97(s,2H), 7.99(q,1H), 7.53(q,1H), 8.78(q,1H) |
| $CHCl_2$ | $CHCl_2$ | H | 74.5–75.5 | 7.10(s,1H), 7.60(s,1H), 8.45(q,1H), 7.64(q,1H), 8.67(q,1H) |
| $CHCl_2$ | $CHCl_2$ | Cl | 76.5–78.5[a] | 6.93(s,1H), 7.66(s,1H), 8.44(d,1H), 7.57(d,1H) |
| $CCl_3$ | $CHCl_2$ | H | 113–118[b] | 7.96(s,1H), 8.59(q,1H), 7.58(q,1H), 9.08(q,1H) |
| $CCl_3$ | $CHCl_2$ | Cl | 41–45[c] | 7.78(s,1H), 8.53(d,1H), 7.67(d,1H) |
| $CHCl_2$ | $CCl_3$ | Cl | 102.5–105.5[d] | 7.65(s,1H), 8.32(d,1H), 7.42(d,1H) |

[a] 98 area % by glc; recrystallization from hexane
[b] 97 area % by glc; purification by TLC
[c] 98 area % by glc
[d] 96 area % by glc; recrystallization from hexane

We claim:

1. A 2,3-bis((poly)chloromethyl)pyridine compound of the formula

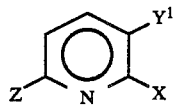

wherein
X and $Y^1$ each, independently represents $CH_2Cl$, $CHCl_2$, or $CCl_3$; and
Z represents hydrogen or chloro;
with the proviso that X and $Y^1$ do not both represent $CH_2Cl$ or $CCl_3$.

2. A compound according to claim 1 wherein X and $Y^1$ represent different moieties.

3. A compound according to claim 2 wherein X represents $CCl_3$ and $Y^1$ represents $CHCl_2$.

4. The compound according to claim 3 wherein Z represents hydrogen.

5. The compound according to claim 3 wherein Z represents chloro.

6. A compound according to claim 2 wherein X represents $CHCl_2$ and $Y^1$ represents $CCl_3$.

7. A compound according to claim 1 wherein X and $Y^1$ each represent $CHCl_2$.

8. The compound according to claim 7 wherein Z represents hydrogen.

9. The compound according to claim 7 wherein Z represents chloro.

10. The compound according to claim 2 wherein X represents $CHCl_2$, $Y^1$ represents $CH_2Cl$, and Z represents hydrogen.

11. The compound according to claim 2 wherein X represents $CH_2Cl$, $Y^1$ represents $CHCl_2$, and Z represents hydrogen.

which comprises contacting 2,3-lutidine with chlorine in the presence of a chlorocarbon diluent in the vapor phase under conditions conducive to the preparation.

13. A process according to claim 12 wherein the process is carried out at temperatures of about 250° to about 550° C., contact times of about 5 to about 120 seconds, chlorine to 2,3-lutidine mole ratios of about 4 to about 16, and chlorocarbon to 2,3-lutidine weight ratios of about 2 to about 50.

14. A process according to claim 13 wherein the process is carried out at temperatures of about 300° to about 450° C., contact times of about 10 to about 30 seconds, chlorine to 2,3-lutidine mole ratios of about 6 to about 12, and chlorocarbon to 2,3-lutidine weight ratios of about 4 to about 30.

15. A process according to claim 12 wherein the chlorocarbon diluent is carbon tetrachloride.

16. A process according to claim 12 wherein X represents $CCl_3$ and Y and Z each represent chloro.

17. A process according to claim 12 wherein X represents $CCl_3$ and Y represents $CHCl_2$.

18. A process according to claim 17 wherein Z represents hydrogen.

19. A process according to claim 17 wherein Z represents chloro.

20. A process according to claim 12 wherein X represents $CHCl_2$ and Y represents $CCl_3$.

21. A process according to claim 12 wherein X and Y each represent $CHCl_2$.

22. A process according to claim 21 wherein Z represents chloro.

23. A process according to claim 21 wherein Z represents hydrogen.

24. A process according to claim 12 wherein X represents $CHCl_2$, Y represents $CH_2Cl$, and Z represents hydrogen.

25. A process according to claim 12 wherein X represents $CH_2Cl$, Y represents $CHCl_2$, and Z represents hydrogen.

* * * * *